US010098601B2

(12) United States Patent
Smith et al.

(10) Patent No.: US 10,098,601 B2
(45) Date of Patent: *Oct. 16, 2018

(54) X-RAY BREAST TOMOSYNTHESIS ENHANCING SPATIAL RESOLUTION INCLUDING IN THE THICKNESS DIRECTION OF A FLATTENED BREAST

(71) Applicant: Hologic, Inc., Marlborough, MA (US)

(72) Inventors: Andrew P. Smith, Lexington, MA (US); Jay A. Stein, Boston, MA (US); Ken Defeitas, Patterson, NY (US); Ian Shaw, Yorktown Heights, NY (US); Zhenxue Jing, Chadds Ford, PA (US); Lauren Niklason, N. Tetonia, ID (US); Baouri Ren, Andover, MA (US); Christopher Ruth, Boxford, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,713

(22) Filed: May 17, 2017

(65) Prior Publication Data

US 2017/0245818 A1     Aug. 31, 2017

Related U.S. Application Data

(63) Continuation of application No. 15/027,650, filed as application No. PCT/US2014/059939 on Oct. 9,
(Continued)

(51) Int. Cl.
*A61B 6/04* (2006.01)
*A61B 6/00* (2006.01)
(Continued)

(52) U.S. Cl.
CPC .............. *A61B 6/502* (2013.01); *A61B 6/025* (2013.01); *A61B 6/04* (2013.01); *A61B 6/0414* (2013.01);
(Continued)

(58) Field of Classification Search
CPC ......... A61B 6/502; A61B 6/025; A61B 6/102; A61B 6/5205; A61B 6/4291; A61B 6/107;
(Continued)

(56) References Cited

U.S. PATENT DOCUMENTS 7,760,924 B2    7/2010  Ruth
8,787,522 B2 *  7/2014  Smith .................... A61B 6/025
                                               378/37
(Continued)

FOREIGN PATENT DOCUMENTS

EP         2366172          9/2011

OTHER PUBLICATIONS

Extended European Search Report issued by the European Patent Office dated Mar. 16, 2017 in connection with European Application No. EP 11831518.
(Continued)

*Primary Examiner* — Courtney Thomas
(74) *Attorney, Agent, or Firm* — Cooper & Dunham LLP

(57) ABSTRACT

Systems and methods for breast x-ray tomosynthesis that enhance spatial resolution in the direction in which the breast is flattened for examination. In addition to x-ray data acquisition of 2D projection tomosynthesis images ETp1 over a shorter source trajectory similar to known breast tomosynthesis, supplemental 2D images ETp2 are taken over a longer source trajectory and the two sets of projection images are processed into breast slice images ETr that exhibit enhanced spatial resolution, including in the thickness direction of the breast. Additional features include breast CT of an upright patient's flattened breast, multi-mode tomosynthesis, and shielding the patient from moving equipment.

20 Claims, 9 Drawing Sheets

Related U.S. Application Data 2014, now Pat. No. 9,668,711, which is a continuation-in-part of application No. 13/253,728, filed on Oct. 5, 2011, now Pat. No. 8,787,522.

(60) Provisional application No. 61/888,825, filed on Oct. 9, 2013, provisional application No. 61/390,053, filed on Oct. 5, 2010.

(51) Int. Cl.
    *A61B 6/02* (2006.01)
    *G06T 11/00* (2006.01)
    *A61B 6/10* (2006.01)

(52) U.S. Cl.
    CPC .............. *A61B 6/102* (2013.01); *A61B 6/107* (2013.01); *A61B 6/4291* (2013.01); *A61B 6/4435* (2013.01); *A61B 6/466* (2013.01); *A61B 6/5205* (2013.01); *A61B 6/5223* (2013.01); *G06T 11/005* (2013.01); *G06T 11/006* (2013.01); *A61B 6/54* (2013.01); *G06T 2211/436* (2013.01)

(58) Field of Classification Search
    CPC ......... A61B 6/04; A61B 6/5233; A61B 6/466; A61B 6/4435; A61B 6/0414; G06T 11/005; G06T 11/006; G06T 2211/436
    See application file for complete search history.

(56) References Cited

U.S. PATENT DOCUMENTS

| | | |
|---|---|---|
| 9,668,711 B2 * | 6/2017 | Smith .................... A61B 6/025 |
| 2003/0194050 A1 | 10/2003 | Eberhard |
| 2005/0084073 A1 | 4/2005 | Seppi |
| 2005/0113681 A1 | 5/2005 | DeFreitas |
| 2007/0223651 A1 | 9/2007 | Wagenaar |
| 2009/0154787 A1 | 6/2009 | Bertram |
| 2012/0114095 A1 | 5/2012 | Smith |
| 2012/0238870 A1 | 9/2012 | Smith |

OTHER PUBLICATIONS

Extended European Search Report issued by the European Patent Office dated Jun. 6, 2017 in connection with European Application No. EP14852393.

* cited by examiner

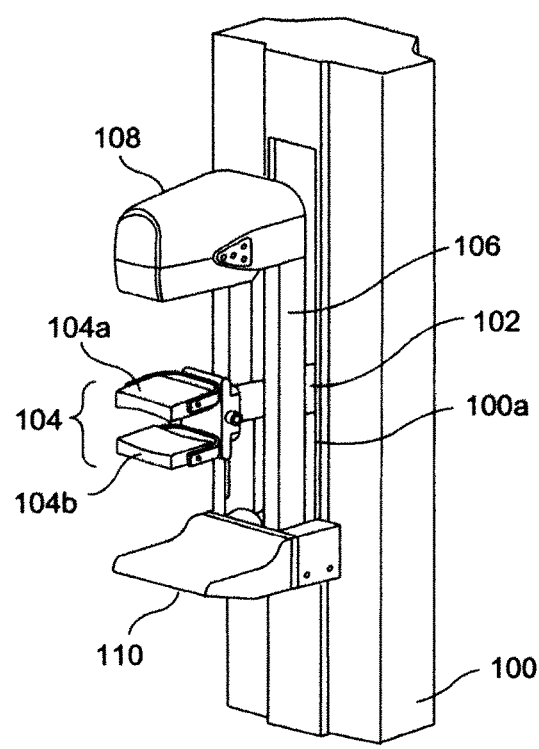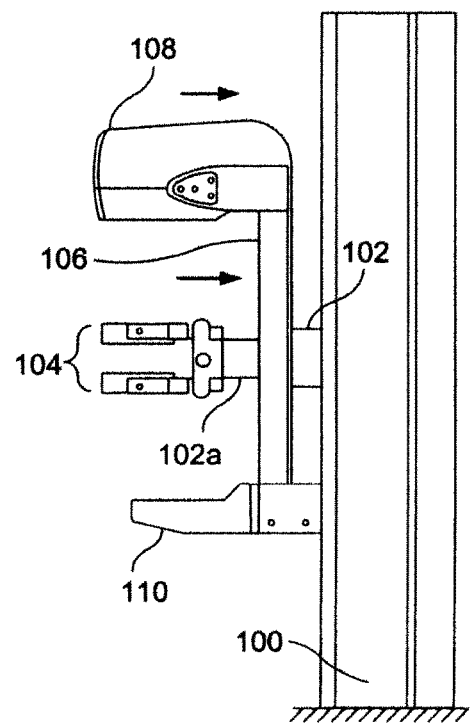
F I G. 1
F I G. 2

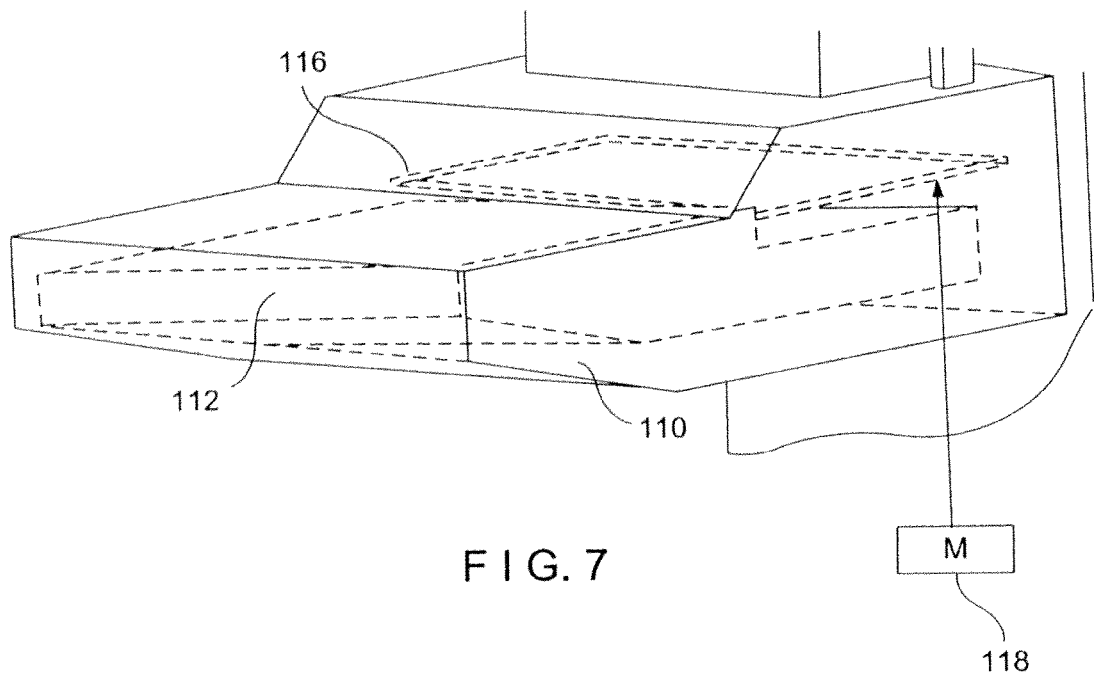
F I G. 7
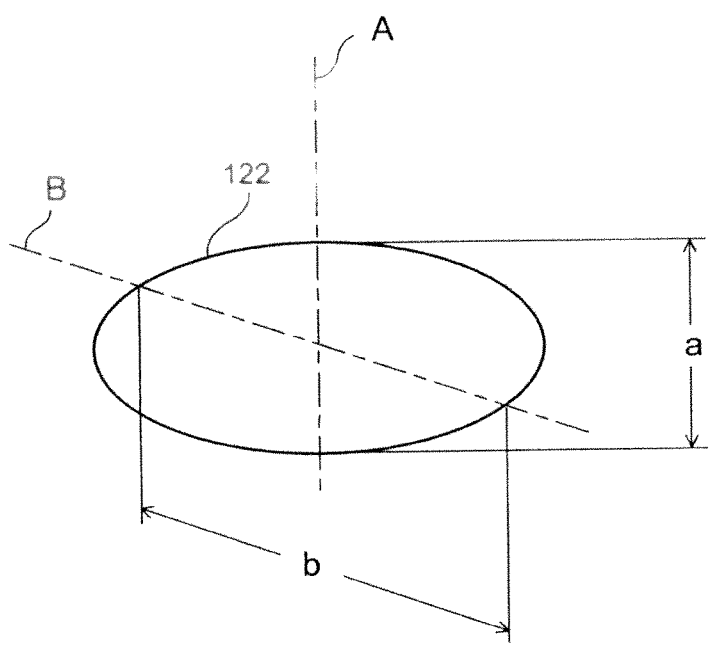
F I G. 8

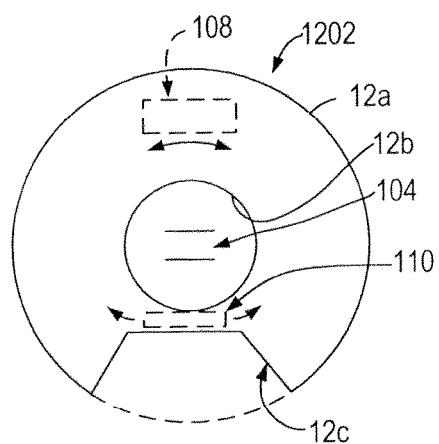 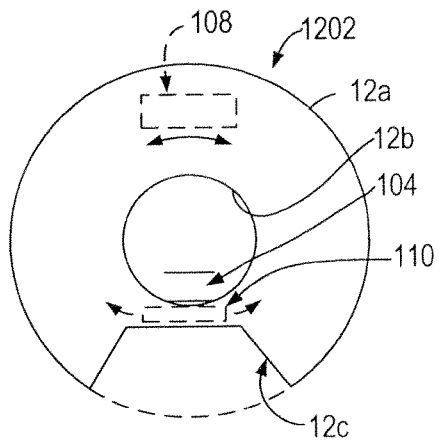
FIG. 12  FIG. 15
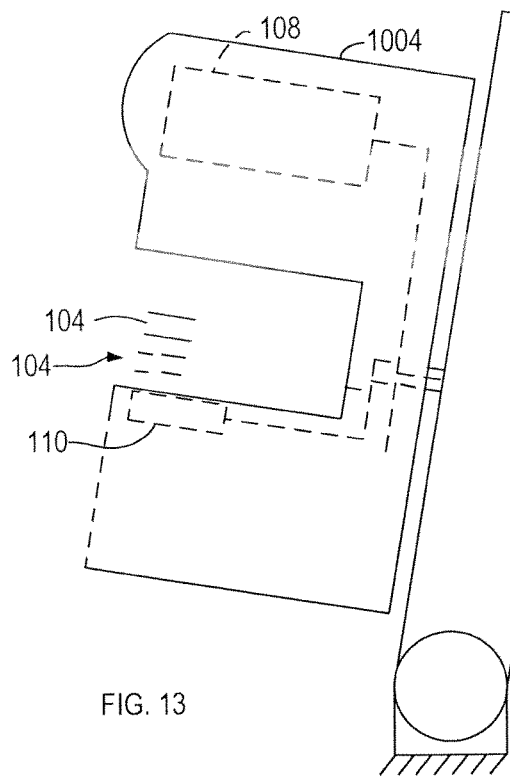 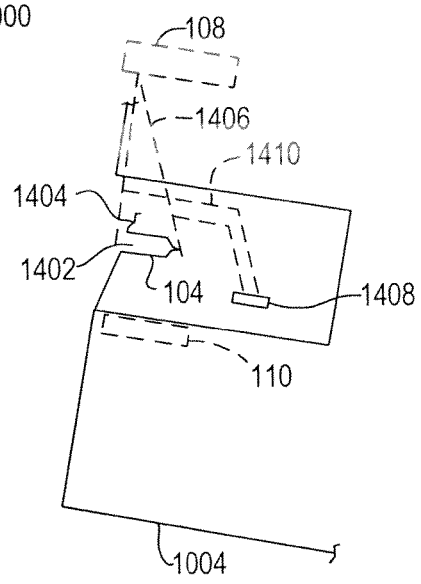
FIG. 13  FIG. 14

X-RAY BREAST TOMOSYNTHESIS ENHANCING SPATIAL RESOLUTION INCLUDING IN THE THICKNESS DIRECTION OF A FLATTENED BREAST

CROSS-REFERENCE TO RELATED APPLICATIONS

This application is a continuation of application Ser. No. 15/027,650 filed on Apr. 6, 2016, which is a national stage filing of PCT/US2014/059939 filed Oct. 9, 2014, which claims the benefit of U.S. provisional application No. 61/888,825 filed Oct. 9, 2013, and is a continuation-in-part of U.S. application Ser. No. 13/253,728 filed Oct. 5, 2012 now U.S. Pat. No. 8,787,522 issued on Jul. 22, 2015 and claiming the benefit of U.S. provisional application No. 61/390,053 filed Oct. 5, 2011. This application incorporates by reference the contents of the foregoing patent applications and claims the benefit of their filing date with respect to the subject matter disclosed therein.

FIELD

This patent specification pertains to x-ray imaging of the breast and more particularly to enhancing the spatial resolution of 3D x-ray breast tomosynthesis images including in a thickness direction of a flattened breast. Additional aspects pertain to multi-mode x-ray breast imaging including multi-mode tomosynthesiss, CT of a flattened breast, and mammography, to related processing of x-ray measurements, and to shielding the patient from moving parts of the equipment.

BACKGROUND OF THE TECHNOLOGY

Breast cancer remains a major health issue implicating a need for early and accurate detection. X-ray imaging has long been used as a gold standard for both screening and diagnosis. The traditional x-ray modality was mammography "M," in which the breast is compressed and flattened and a projection x-ray image "Mp" is taken using an x-ray source at one side of the breast and an imaging receptor at the other side, usually with an anti-scatter grid between the breast and the receptor. The receptor for many years was x-ray film, but now digital flat panel imaging receptors have become prevalent.

X-ray breast tomosynthesis "T" has made important inroads, with the widespread acceptance in this country and abroad of systems offered over the last several years by the common assignee, including under the tradename Selenia® Dimensions®. In this modality, the breast also is compressed and flattened but at least the x-ray source moves around the compressed breast and the image receptor takes a plurality of projection images "Tp," each at a respective angle of the imaging x-ray beam to the breast. The Dimensions® system operates in the tomography mode T to rotate an x-ray source around the patient's flattened breast while a flat panel imaging x-ray receptor takes respective 2D projection tomosynthesis images Tp for each increment of rotation angle over a trajectory that is substantially less than 180°. As one example, the trajectory extends over ±7.5° relative to a 0° position that can but need not be the same as the CC or the MLO position in conventional mammography M. The system processes the resulting 2D projection images Tp (e.g., 15 images Tp) into a 3D reconstructed image of voxel values that can be transformed into reconstructed slice images "Tr" each representing a slice of the breast that has a selected thickness and orientation. Tomosynthesis systems offered by the common assignee respond to operator control to operate in an additional, mammography mode M to produce mammogram images Mp that can be the same as or similar to conventional mammograms. In addition, some of the systems synthesize a mammogram from the reconstructed 3D image of the breast or from images Tr.

Examples of known T and M modes of operation are discussed in U.S. Pat. Nos. 4,496,557, 5,051,904, 5,359,637, 6,289,235, 6,375,352, 6,645,520, 6,647,092, 6,882,700, 6,970,531, 6,940,943, 7,123,684, 7,356,113, 7,656,994, 7,773,721, 7,831,296, and 7,869,563; Digital Clinical Reports, Tomosynthesis (GE Brochure 98-5493, November 1998); D G Grant, "Tomosynthesis: a three-dimensional imaging technique", IEEE Trans. Biomed. Engineering, Vol BME-19, #1, (January 1972), pp 20-28; U.S. Provisional Application No. 60/628,516, filed Nov. 15, 2004, the benefit of which is claimed in U.S. application Ser. No. 14/744,930 filed on Jun. 19, 2015 and entitled "Matching geometry generation and display of mammograms and tomosynthesis images;" a system announced under the name Giotto Image 3D by I.M.S. Internazionale Medico Scintifica of Bologna, Italy, and a 3D Breast Tomosynthesis system announced by Siemens Healthcare of Germany/USA. Several algorithms for reconstructing slice images from tomosynthesis projections are known, including filtered back-projection and matrix inversion processing, and a proposal has been made to combine information from both. See Chen Y, Lo, J Y, Baker J A, Dobbins III J T, Gaussian frequency blending algorithm with Matrix Inversion Tomosynthesis (MITS) and Filtered Back Projection (FBR) for better digital breast tomosynthesis reconstruction, Medical Imaging 2006: Physics of Medical Imaging, Proceeding of SPIE Vol. 6142, 61420E, (2006).

Whole-body CT x-ray imaging of a patient's thorax also can provide a 3D image of the breast but delivers ionizing radiation to the chest cavity as well. Also, in whole-body x-ray CT the spatial resolution of the breast tends to be lower than in mammography and tomosynthesis because the image matrix includes the entire chest, not just the breast. Overall x-ray dose to the patient tends to be higher. Other modalities also can generate breast images, such as MRI, emission imaging, thermal imaging, and others, but because of various inherent limitations have not been widely used for breast-only imaging. They typically are not suitable for screening, which demands a set of practical attributes that such system may lack, such as good patient flow, relatively low level of patient inconvenience and time, rapid examination, and relatively low cost per patient for the actual examination and for interpretation of the resulting images. CT x-ray imaging of only the breast has been proposed, and can generate high spatial resolution image but the equipment believed to have been in clinical use requires a special table on which the patient lies in the prone position, with a breast protruding downwardly through a table opening and exposed to a nearly horizontal imaging x-ray beam. The breast is not flattened in a coronal plane, so there are no benefits of flattening that mammograms and tomosynthesis images enjoy, such as spreading out lesions for better imaging and reducing skin x-ray dose per unit area. Examples of breast-only x-ray CT are discussed in U.S. Pat. Nos. 3,973,126, 6,748,044, and 6,987,831, 7,120,283, 7,831,296, 7,867,685 and US application No. 2013/0259193 A1, now U.S. Pat. No. 8,842,406 issued on Sep. 23, 2014, proposes CT scanning a standing patient's breast confined by one or two pairs of opposing compression paddles.

SUMMARY OF THE DISCLOSURE

This patent specification describes an advance in x-ray breast tomosynthesis that increases spatial resolution, including in the thickness direction of a flattened breast, without incurring the expense and radiation dose increase of known whole-body CT and even breast-only CT. The new approach, which this patent specification labels enhanced tomosynthesis "ET," takes a first series of projection images "ETp1" that can be similar or identical to that currently used in said Dimensions® systems but, in addition, takes supplemental 2D tomosynthesis projection images "ETp2" from imaging positions that can be angularly spaced more coarsely but over a longer source trajectory, or otherwise differ from images ETp1, and uses both images ETp1 and ETp2 in reconstructing an improved 3D image of the breast and improved Tr images of breast slices.

Images ETp1 can be taken at any time relative to images ETp2, such as before or after, and even interleaved in time and/or space/angle. The x-ray source trajectories for taking images ETp1 and ETp2 can be over different arcs around the flattened breast that may or may not overlap, or the trajectory for the ETp2 images may encompass the entire trajectory for the ETp1 images. As a non-limiting example, the source trajectory arc for images ETp1 can be ±7.5° and the source trajectory arc for images ETp2 can be significantly greater. Thus, the trajectory for images ETp2, can be a continuous or discontinuous arc totaling up to and including 180° plus the angle of the imaging x-ray beam in the plane of source rotation, and can even be up to and including 360° (possibly plus the beam angle). Shielding the patient from moving components and yet allowing good access of the breast to the imaging space can be a challenge that is more manageable if the source trajectory is significantly less than 360°. The patient x-ray dose for images ETp1 can be comparable to currently available tomosynthesis or can be lowered so that the total dose, when images ETp2 are included, is substantially the same or only marginally greater that for the Tp images in the currently available Dimensions® system, but still is significantly less than for whole body CT and even breast-only CT.

In addition to the new mode ET, this patent specification describes a multi-mode breast x-ray tomosynthesis method Tmm, which is a variation of the T mode in which the system selectively uses either a narrow angle sub-mode Tn or a wide angle sub-mode Tw. The two sub-modes differ from each other in the angular extent of the x-ray source arc, but may differ in additional respects as well. More than two sub-modes can be included in the Tmm mode. An anti-scatter grid can be used in one, or more than one, or in all modes of operation, but some modes can be used without such a grid. The grid can be retractable or at least removable so that some modes can use a grid and some may not in the otherwise same or similar equipment.

This patent specification still further describes a breast-only CT system for imaging a flattened breast of an upright patient, and also describes a mammography mode M that can be included in a multi-mode breast x-ray system.

This patent specification still further describes ways of shielding the patient from moving elements of the system that are uniquely matched to the new breast imaging modes to meet the challenges of good physical protection, good access of the breast to the imaging space, and good access for the health professional in positioning the breast and adjacent tissue for flattening and imaging.

BRIEF DESCRIPTION OF THE DRAWING

FIG. 1 is a perspective view of components of a multi-mode breast x-ray imaging system useful for operating in an enhanced tomosynthesis mode ET, narrow angle and wide angle tomosynthesis modes Tn and Tw, a breast-only CT mode for an upright patient, and a mammography mode M.

FIG. 2 is a side elevation of the system of FIG. 1.

FIG. 7 is a perspective view illustrating an imaging receptor that can pivot inside the receptor housing.

FIG. 8 is a schematic illustration of different path lengths of x-rays through a flattened breast of a patient.

FIGS. 12-15 illustrate another alternative embodiment that is particularly suited for imaging modes that include ET and CT but also is useful for T mode (including Tmm), and M modes.

DETAILED DESCRIPTION OF PREFERRED EMBODIMENTS

Figure 4:
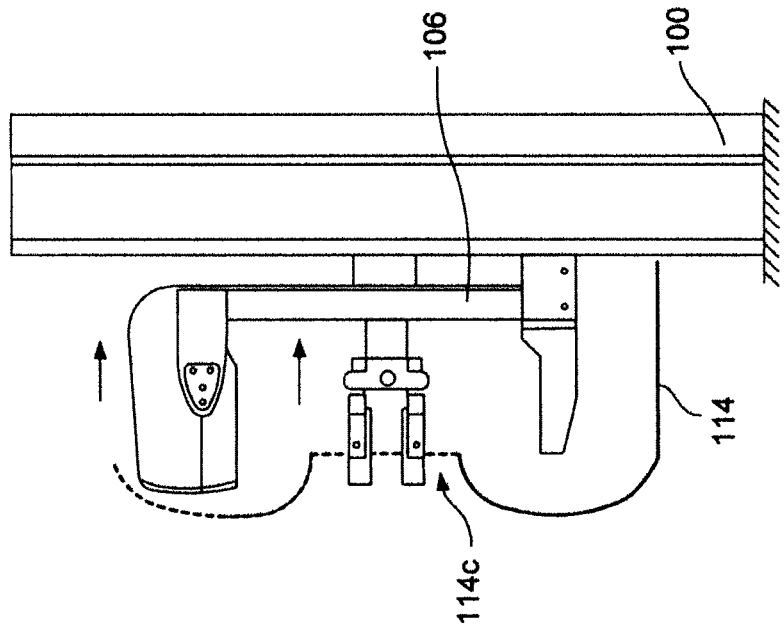
FIG. 4 is a side elevation that is otherwise the same as FIG. 2 but illustrates a patient shield.

FIGS. 1 and 2 illustrate basic elements of a breast x-ray imaging system operable in any one of several modes to image a flattened breast of a patient. Essentially the same equipment can operate in one of two or more of the modes. The modes include: (a) an enhanced tomosynthsis mode ET that brings about improved spatial resolution, including in the thickness direction of a flattened breast; (b) a breast-only CT mode in which the patient is upright and the breast is flattened for imaging; (c) a tomosynthesis mode T that can include a multi-mode tomosynthesis Tmm that comprises a wide angle tomosynthesis mode Tw and/or a narrow angle tomosynthesis mode Tn; and (d) a mammography mode M. Depending on the mode, elements may be added to or removed from the configuration of FIGS. 1 and 2 as described below. The mode selection can be in response to commands from a user or from some other source or by settings by the manufacturer or the facility using the system.

Referring to FIGS. 1 and 2, a support column 100 is secured to a floor and houses a motorized mechanism for raising and lowering a horizontally extending axle 102 protruding through an elongated opening 100a in column 100, and for rotating axle 102 about its central axis. Axle 102 in turn supports a coaxial axle 102a that can rotate with or independently of axle 102. Axle 102 supports a breast immobilization unit 104 comprising an upper plate 104a and a lower plate 104b such that (i) both plates can move up and down along the long dimension of support 100 together with axles 102 and 102a, (ii) at least one of the plates can move toward and away from the other, (iii) unit 104 can rotate about the common central axis of axles 102 and 102a, and (iv) axle 102a can move in the horizontal direction relative to axle 102 to thereby change the distance between immobilization unit 104 and column 100. In some modes, breast immobilization unit 104 compresses the breast between upper place 104a and the top surface of receptor housing 110

(in which case the system need not include lower plate 104b). In addition, axle 102 supports a gantry 106 for two types of motorized movement: rotation about the central axis of axle 102, and motion relative to axle 102 along the length of gantry 106. Gantry 106 carries at one end an x-ray source such as a shrouded x-ray tube generally indicated at 108, and at the other end a receptor housing 110 enclosing an imaging x-ray receptor 112 (FIG. 7).

Figures 5, 6:
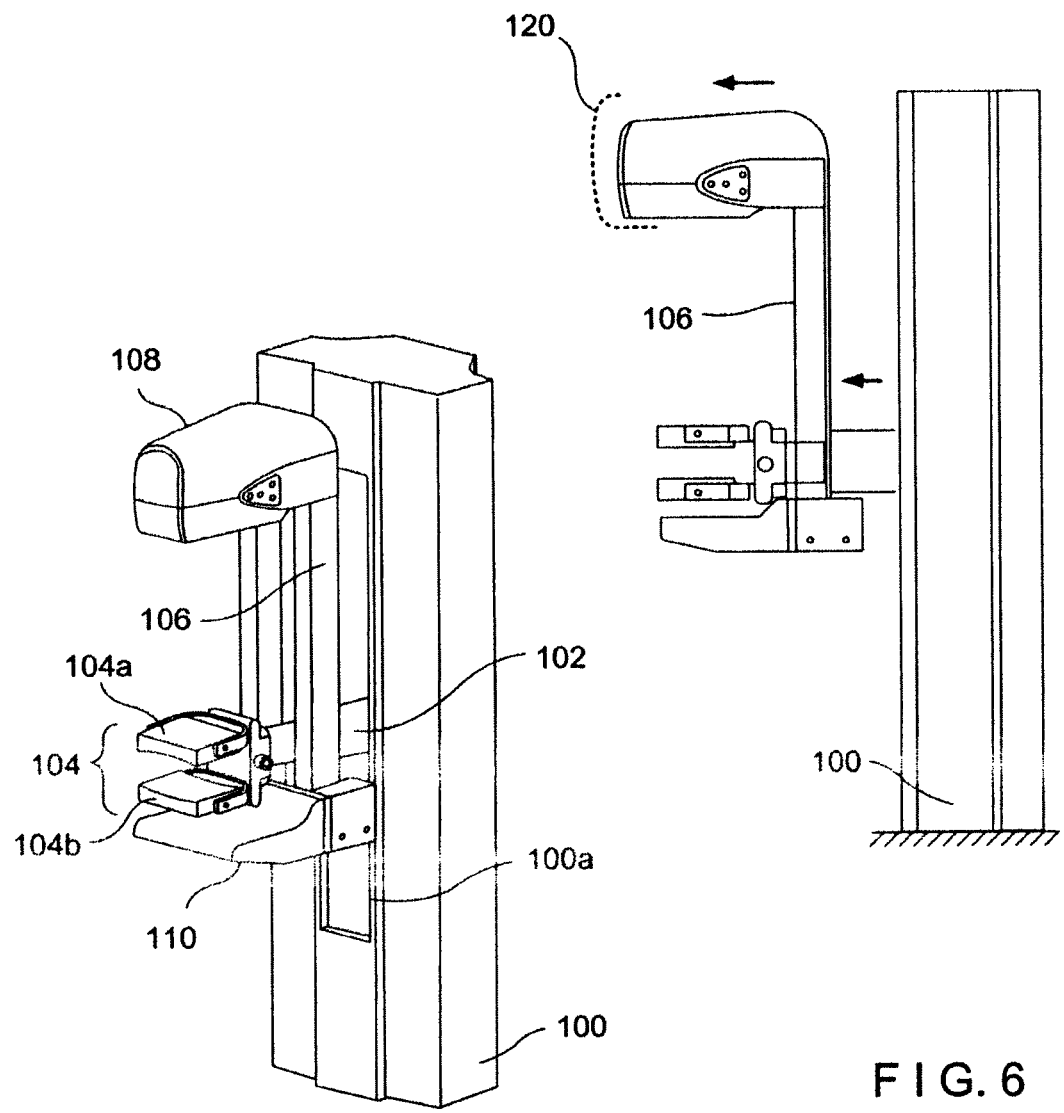
FIGS. 5 and 6 are similar to FIGS. 1 and 2, respectively, but illustrate the system as used in tomosynthesis modes or a mammography mode.

For operation in different modes, elements can be added or removed from the system of FIGS. 1 and 2, as described below. For example, for operating in mode M, only the upper compression plate 104 need remain, and the patient's breast can be flattened between plate 104a (serving as a compression paddle) and the top surface of receptor housing 110 (one or both of which may be covered with a pliable pad or covering to assist in patient comfort). For operation in one of the T and Tmm modes, again the breast can be flattened between top plate 104a and the top surface of receptor housing 110, which in this case includes, as illustrated in FIG. 7, an imaging receptor 112 that rocks in synchronism with motion of source 108 around the flattened breast. In the ET mode, and alternatively in the T mode (including the Tmm mode), the breast can be compressed between plates 104a-104b and, as illustrated in FIGS. 5-6, source 108 and receptor housing 110 can rotate around unit 104. In this case, receptor 112 can be fixed relative to receptor housing 110. In some or all of the modes, patient shielding can be added to protect the patient from moving parts of the system, as discussed below, which can be particularly important in the ET and CT modes although shielding also can be important in the T (including Tmm) modes and in M mode.

In the ET mode, the patient's breast is flattened between compression plates 104a and 104b. X-ray source 108 rotates about the flattened breast through a first trajectory, and imaging receptor 112 shrouded in housing 110 takes a succession of tomosynthesis projection images ETp1, while rotating through the same or similar arc around the breast. With the patient's breast remaining in place, source 108 rotates through a second trajectory and receptor 112 takes a second series of tomosynthesis projection images ETp2, while also rotating around the breast. For example, the first trajectory is through an arc of ±7.5° relative to a line normal to the top surface of receptor housing 110, while the second trajectory is through an arc that totals 180° plus the imaging beam angle, e.g., a total of approximately 200°. As an alternative, Images ETp1 can be taken either while receptor housing 110 is fixed in space but receptor 112 optionally rocks, or images ETp1 can be taken while source 108 and receptor housing both rotate about immobilization unit 104 (and receptor 112 need not rock). Images ETp2 are taken while both source 108 and receptor housing 110 rotate, for example through arcs that include the positions illustrated in FIG. 3. The two series of images ETp1 and ETp2 can be taken in any order. The arcs for the first and second series of images can encompass angles different from those stated above, and can be distributed at places around the breast that are different from those stated above. The total angles of the arcs also can be different. And, the direction in which the breast is flattened need not be the vertical direction as illustrated but can be any other desired direction, including the direction used for MLO imaging in conventional mammography. For example, if the source trajectory for images ETp1 is ±7.5° and the source trajectory for images ETp2 is 200°, in a CC orientation of the breast the trajectory for images ETp1 can be at the center of the trajectory for images ETp2, and no images ETp2 would be taken where the two trajectories overlap, as the information is already available from images ETp1.

The patient x-ray dose per projection image ETp2 can be lower than per projection image ETp1. In addition, the angular spacing for projection images ETp2 can be greater than for projection images ETp1. For example, an image ETp1 can be taken for each 1° of motion of source 108 around the flattened breast while an image ETp2 can be taken for each 2°, or 3°, or a greater interval of motion of source 108 around the breast.

Figure 9:
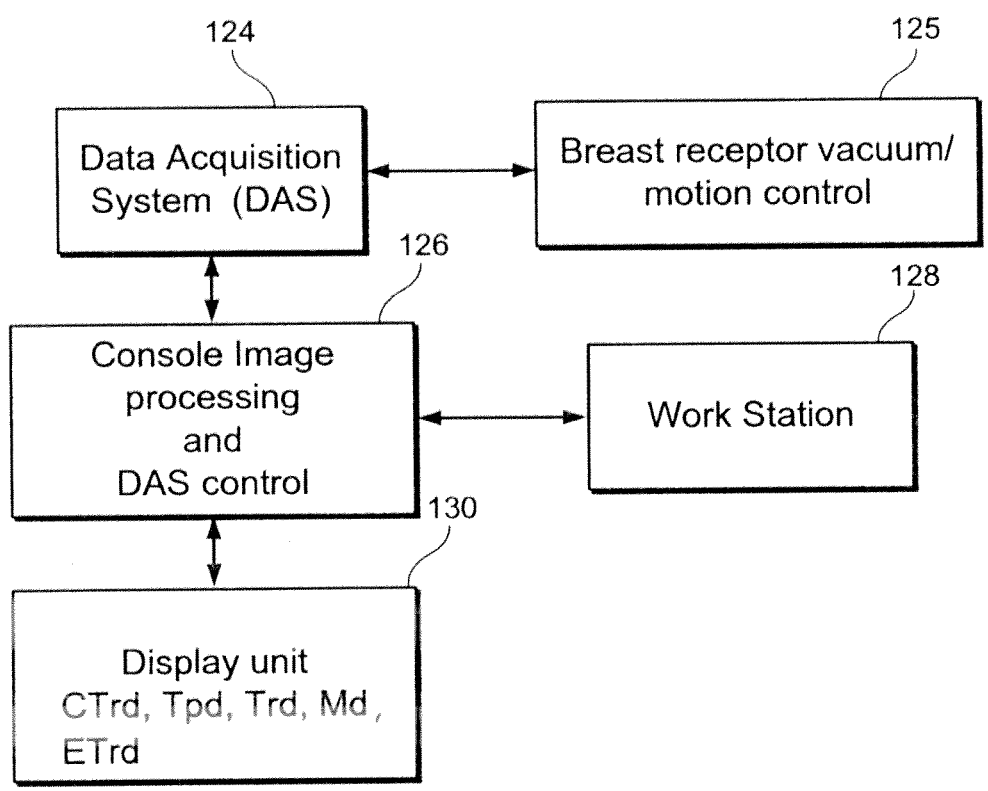
FIG. 9 is a block diagram illustrating an integrated x-ray system that can operate in any one of several imaging modes (or only in a single mode).

Notably, in the ET mode the system varies x-ray parameters such as x-ray hardness in relation to angular orientation of the imaging x-ray beam. For example, when the breast is compressed in the vertical direction, as for imaging in the CC orientation, the system uses harder x-rays when the imaging x-ray beam is horizontal. In general, varying hardness relates to the pathlength of the x-rays through the breast. For example, if a breast is flattened such that its thickness in the vertical direction is 6 cm its width in the horizontal direction can be three time that, i.e., 18 cm. Accordingly, the system controls x-ray hardness to make efficient use of radiation that penetrates the breast and is detected at the x-ray receptor. To this end, the system may seek to keep reasonably uniform the photon count for all positions at which images ETp1 and ETp2 are taken, i.e., for each of the images the minimum number of x-ray photons that contribute to a pixel value should be the same or close to the same. This can be achieved in a number of ways. For example, the system can control the voltage of the x-ray tube and thus the hardness of the x-rays that it emits depending on the angular position of the tube with respect to the breast. Alternatively, or in addition, the system can control x-ray dose to the patient with angular position of the x-ray source, such as by controlling parameters such as x-ray tube current (mAs) and the time over which the imaging receptor acquires an image. The discussion below of FIG. 9 provides more detail of such control.

Figure 3:
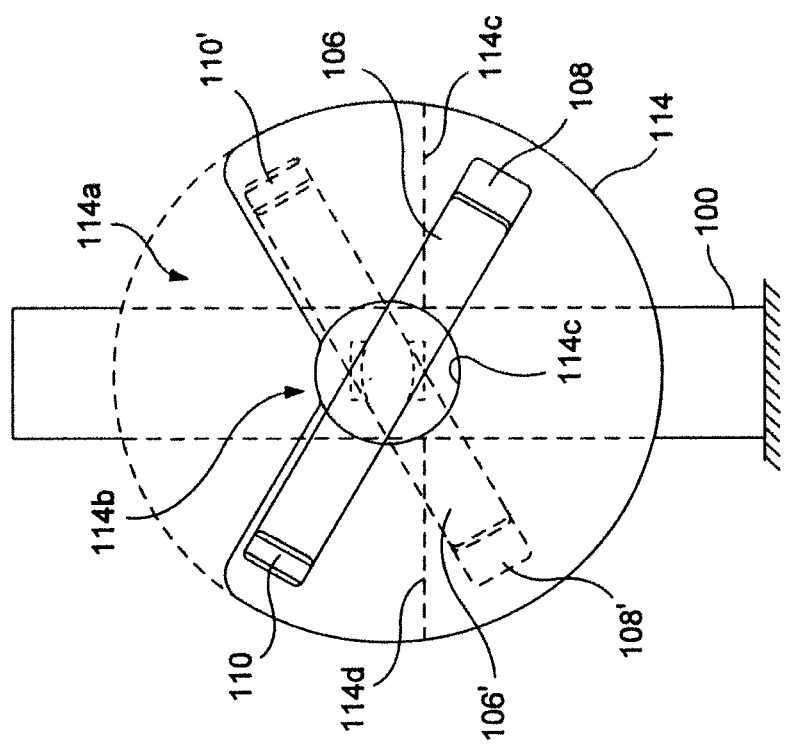
FIG. 3 is a front elevation illustrating a patient shield for a system similar to that seen in FIGS. 1 and 2.

FIGS. 3 and 4 illustrate an example of a system configuration for the ET mode and for a breast-only CT mode for an upright patient. FIG. 3 illustrates a rotating gantry 106 that carries source 108 and receptor housing 110 in a fixed relationship to each other. FIG. 4 is a side elevation otherwise similar to FIG. 2 but additionally shows a patient shield 114 having a central opening 114c. Shield 114 can be completely circular in front elevation, as illustrated by the circle that includes an arc in broken line in FIG. 3. In that case, gantry 106 can rotate through a complete circle in the CT mode, plus possibly the imaging beam angle. As an alternative, shield 114 can leave open a sector or segment 114a illustrated in FIG. 3 as the area below the broken line arc and between the solids lines of shield 114. In that case, gantry 106 can rotate only through an angle that is less than 360°, such as an angle of 200°, but the patient can have space for her head and perhaps an arm and a shoulder in the V-shaped cutout 114b of shield 114, for a more comfortable body posture. Specifically, as illustrated in FIG. 3, gantry 106 can rotate only within the portion of shield 114 that is outside V-shaped cutout 114b. One of the possible positions of gantry 106 and tube 108 and receptor housing 110 is shown in solid lines in FIG. 3. Another possible position is shown in broken lines, and designated as gantry 106', carrying x-ray source 108' and receptor housing 110'. As an alternative to having cutout 114a at the top, as shown in FIG. 3, the cutout can be at the bottom of shield 114. In that case, there would be room for the patient's legs closer to support 100, and the arc of source 108 can include positions in which the source irradiates the patient's breast from above, as in the typical CC and MLO orientations of the breast. This can be preferable particularly when the gantry centerline is tilted away from the patient, as discussed below regarding FIGS. 10 and 11. FIGS. 12-14, which are discussed in more detail below, illustrate an alternative configuration for the ET and CT modes, in which not only the patient's breast but also a patient's arm can be positioned in the imaging field, to thereby facilitate imaging the axilla. The compression force on the breast for T (including Tmm) and CT modes can be less, even considerably less, than the compression force currently used in mammography-only systems or for the mammography mode M in the Selenia® Dimensions® system currently offered by the common assignee.

Figure 3A:
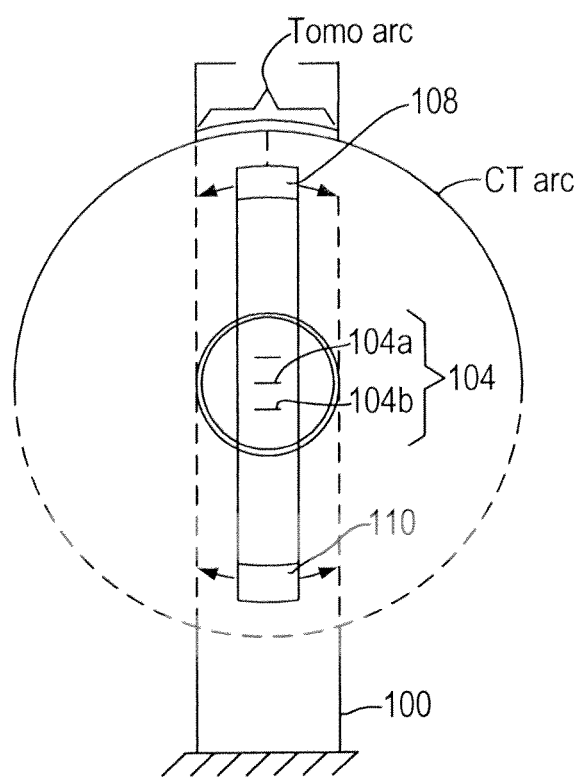
FIG. 3a is an otherwise similar elevation but illustrates a first, narrower angle source trajectory "Tomo arc" and a second, wider angle source trajectory "CT arc" for use in an enhanced tomosymthesis mode of operation.

FIG. 3a illustrates a possible combination of arcs of source 108 for the acquisition of ETp1 and ETp2 images when the system is operating in the ET mode and the breast is in a CC orientation. In this non-limiting example, the system acquires the ETp1 images while source 108 traverses the arc labeled "Tomo arc" that can extend about 15° around the breast, and acquires the images ETp2 while source 108 traverses an arc of about 200° labeled "CT arc." Images ETp1 can be acquired at relatively low kV (soft x-rays such as in the range of 20-40 kV) but relatively high dose while images ETp2 can be acquired relatively high kV, such as 50-80 kV) but lower dose. Where the two arcs overlap, only ETp1 images can be acquired, or both ETp1 and ETp2 images can be acquired. The breast can be schematically shown in an oval shape in a coronal section, but is should be understood that the flattened (non-cylindrical) shape of the breast used in the system of this patent specification can be defined by appropriately shaping the breast support and compression surfaces of immobilization unit 104.

FIG. 4 illustrates a possible shape of patient shield 114 in side elevation. Shield 114 bulges away from central opening 114c in a direction away from column 100, to allow the patient's breast to reach into and become immobilized in unit 104 while the shield 114 separates the patient's body from the rotating components, namely gantry 106 and x-ray source 108 and receptor housing 110. Opening 114c can be made larger, and can be shaped differently from the illustration in FIGS. 3 and 4 (which are not to scale) to facilitate access by the x-ray technician to the patient's breast as the breast is being flattened. Portions of shield 114 can be removable or hinged to further facilitate access. For example, one or both of the portions of shield 114 above broken lines 114d and 114e (FIG. 3) can be removable or hinged such that they can be moved out of the way while the technician is positioning and immobilizing the patient's breast, and put back to protect the patient before scanning in the ET or CT mode starts. Patient shield 114 can be mounted on column 100 and/or the floor. In the example of FIG. 4, the rotating gantry 106 can be moved to the left or to the right so that it is closer to or further away from the patient, i.e., from one to the other of the position seen in FIG. 4 and the position seen is FIG. 6. Thus, for ET or CT imaging of the breast using the example of FIG. 4, rotating gantry 106 is spaced away from column 100, to the position relative to column 100 illustrated in FIG. 6, and actually imaging the patient's breast only while the receptor housing 110 is outside the cutout 114b. Thus, the patient can lean forward, partly into cutout 114b so that more of the beast being imaged, and possibly surrounding tissue, can come into the x-ray imaging field.

In the tomosynthesis mode T, the system can generate images in the same manner as images ETp1 are generated. The narrow angle sub-mode Tn and the wide angle sub-mode Tw differ from each other in the angular extent of the trajectory of x-ray source 108 and may or may not differ in additional ways as well. For example, they may differ in the number of tomosynthesis projection images Tpn and Tpw that receptor 112 produces during a single sweep through the source trajectory. Typically but not necessarily images Tpw are greater in number that images Tpn for a single imaging sweep of source 108. There can be additional sub-modes that differ from Tn and Tw in the extent of the trajectory of source 108 and possibly in other respects, but still are tomosynthesis modes.

FIGS. 5-7 illustrate operation in mode T, including sub-modes Tn and Tw, and some aspects of mode ET. FIGS. 5 and 6 are otherwise the same as FIGS. 1 and 2 respectively, except that gantry 106 is in a different position relative to breast immobilization unit 104 and axle 102 and column 100. In particular, x-ray source 108 is further from unit 104 and column 100, and receptor housing 110 is closer to unit 104. In mode T (including Tmm) as shown in FIGS. 5 and 6, the patient's breast is immobilized and flattened between plates 104a and 104b, which remain in place during imaging. Alternatively, plate 104b is removed and the breast is compressed between plate 104a and the upper surface of receptor housing 110. In one example, in which the breast is compressed between plates 104a and 104b, x-ray tube 108 and receptor housing 110 may undergo a rotation about the immobilized breast through an angle less than 180°, such as ±15° or ±7.5° relative to a 0° position, which can but need not be the same as conventional CC and MLO positions in mammography. A respective two-dimensional projection image Tp is taken for each increment of rotation while x-ray source 108 and imaging receptor 112 inside housing 110 rotate as a unit, fixed with respect to each other, as illustrated in commonly owned U.S. Pat. No. 7,123,684, incorporated by reference. Alternatively, the motions of x-ray tube 108 and receptor 112 relative to the immobilized breast can be as illustrated in commonly owned U.S. Pat. No. 7,616,801. In this alternative case, x-ray tube rotates about the central axis of axle 102, but receptor housing 110 remains in place while imaging receptor 112 pivots or rocks inside housing 110 about an axis that typically passes through the image plane of the receptor, is parallel to the central axis of axle 102, and bisects imaging receptor 112. The pivoting or rocking of receptor 112 typically is through a smaller angle than the rotation angle of x-ray tube 108, calculated so that a normal to the imaging plane of receptor 112 can continue pointing at or close to the focal spot in x-ray tube 108 from which the imaging x-ray beam is emitted, and so that the beam continues to illuminate all or most of the imaging surface of receptor 112. In one example of mode T, x-ray tube 108 rotates through an arc of about ±7.5° while imaging receptor rotates or pivots through about ±5° about the horizontal axis that bisects its imaging surface. During this motion, a plurality of projection images Tp are taken, such as 15 images, at increments of rotation angle that can be uniform or not uniform. The central angle of the arc of the trajectory of x-ray source 108 can be the 0° angle, i.e., the position of the x-ray source 108 seen in FIGS. 5 and 6, or some other angle, e.g., the angle for the x-ray source position typical for MLO imaging in conventional mammography. Other arc angles and number of a Tp images are possible, such as ±15° and 20-21 images.

The examples of angles of rotation of x-ray source 108 in the Tn and Tw sub-modes are not limiting. The important point is to provide multiple versions of mode Tmm where one selection involves x-ray source rotation through a greater angle around the breast than another selection.

Essentially the same equipment can be configured to provide more sub-modes of mode T; for example, there can be three or more sub-modes each using a respective trajectory of source 108 that encompasses a respective different angle of rotation or other motion around unit 104.

The system illustrated in FIGS. 5 and 6 also can operate in an enhanced tomosynthesis mode ET to thereby increase spatial resolution of 3D images of the breast. In the ET mode, x-ray source 108 moves along a first trajectory around the flattened breast that can but need not be the same as in mode T, but in addition moves through a second trajectory around the breast. In the course of each trajectory, imaging receptor 112 generates 2D tomosynthesis projection images Tp for respective position of the source in its trajectory. As discussed below in connection with FIG. 9, the system blends information from images ETp1 and ETp2 to produce a 3D image of the breast with increased spatial resolution particularly in the thickness direction of the flattened breast compared with using only the ETp1 images. Preferably, the arc of source 108 for images ETp2 is 180° plus the beam angle, i.e, a total of about 200°, centered on the arc for images ETp1, but does not include images ETp2 over the arc in which images ETp1 are taken. In the more general sense, the second trajectory can inscribe an arc of an angle that is the same as, larger than, or smaller than for the first trajectory, and can take place before or after the first trajectory, or parts of the first and second trajectories can alternate. For example, if the first trajectory total arc is 7.5°, the second trajectory arc can be 30°, 60°, or 180°, or some other angle greater than 7.5°. In that case, the angular spacing of source positions in the second trajectory can be generally greater than in the first trajectory, and need not be constant throughout the second trajectory. For example, the number of ETp1 and ETp2 images can be the same when the total angle of the second trajectory is twice or more times the angle of the first trajectory. Alternatively, the angle of the second trajectory can be the same as or smaller than the angle of the first trajectory, but the first and second trajectories would inscribe non-coincident arcs around the flattened breast or arcs that are angularly spaced from each other. As discussed below, in the ET mode the system blends contributions from the ETp1 and ETp2 images in a tomosynthesis image reconstruction process to generate a 3D image of the breast and reconstructed slice images Tr and display images "Trd."

As in the T and Tmm modes, in the ET mode the breast can be flattened in unit 104 but, alternatively, lower plate 104b may be removed so that the breast is supported between the upper surface of receptor housing 110 and upper plate 104a, in a manner analogous to the way the breast is immobilized in said system currently offered under the tradename Dimensions®, so long as the imaging receptor can generally follow the rotation of the x-ray source.

In the CT mode, the system of FIGS. 1 and 2 flattens and immobilizes the breast of a standing or sitting patient between plates 104a and 104b, source 108 and receptor housing 110 rotate around the breast over a CT angle that typically is 360° plus possibly the imaging beam angle, or is at least 180° plus the imaging beam angle, and imaging receptor 112 produces 2D projection images CTp for each increment of rotation. The images CTp are processed into a 3D image of the breast, which can be represented as reconstructed images CTr of breast slices.

In the M mode, the system of FIGS. 1 and 2 flattens the patient's breast between upper plate 104a and the top surface of receptor housing 110 (and dispenses with lower plate 104b). Source 108, receptor housing 110 (and receptor 112), and plate 104a can rotate as a unit to an orientation such as for CC or MLO imaging before the breast is flattened. With source 108 and receptor 112 stationary, and the breast flattened and immobilized, the system takes a mammogram Mp that is similar to a conventional mammogram.

Concave plates 104a and 104b can be used, or generally flat plates can be substituted, or a single flat or concave compression paddle can be used to flatten a breast supported by the upper surface of receptor housing 110. In some or all of the modes, the coronal cross-section of the breast immobilized in unit 104 can be approximately elliptical, as illustrated for breast 122 in FIG. 8, or mostly elliptical but with flat areas on top and/or bottom, such that the width of the immobilized or compressed breast 122 is significantly more than its thickness. In that case, as seen in FIG. 8, the path length "a" along line "A" through breast 122 is shorter than path length "b" along line B for x-rays within the imaging beam. An alternative involves using for at least one of plates 104a and 104b a plate made of a material that is sufficiently flexible/bendable to reduce the thickness of the compressed breast and yet yield somewhat to the breast shape to improve patient comfort.

It can be desirable to vary the spectrum of the x-rays with angle of the imaging x-ray beam relative to the breast. For example, softer x-rays can be used for path "a" than for path "b" in FIG. 8 in order to improve the x-ray image. To this end, the system when used in the CT mode or in the T (including Tmm), or ET modes, with a breast 122 flattened to a cross-section that is significantly wider that thick, can be operated under computer control to vary the x-ray beam hardness accordingly, for example by varying the voltage (kV) driving x-ray tube 108. The arrangement can be set to make the x-rays hardest where they pass through the greatest length of breast tissue (horizontal direction in a CC orientation of the breast) and progressively softer toward where they pass through the least thickness (vertical direction in the CC orientation of the breast), also taking into account the inherent heel effect of x-ray beams that x-ray tubes generate.

FIG. 9 illustrates a system that processes and displays images resulting from the operation of a data acquisition system 124 that includes x-ray source 108 and imaging receptor 112 operating in one or more of the modes described above. These images are provided to a console 126 that includes an image processing unit configured to computer-process the projection images ETp1 and ETp2 in the ET mode, Tp in the T mode (and Tnp and Twp in the Tmm mode), CTp in the CT mode, and Mp in the M mode, into image data for respective reconstructed slice images ETr, Tr, and CTr, and display images ETrd, Trd, CTrd, and Md for viewing. In addition, console 126 controls data acquisition system 124 to operate as described above. For clarity and conciseness, conventional elements such as power supplies, operator controls and safety devices, are not illustrated. For images Tp and projection images in the Tmm mode (including Tnp and Twp) and mammograms Mp, the operation of console 126 can be similar or identical to that used in said system offered under the Dimensions® trade name, or as discussed in said references cited above. For CTr images, the computer processing can operate as discussed in said U.S. Pat. No. 6,987,831. It is believed that superior results in image interpretation result when a combination of different images of a breast are presented to the image reader, preferably but not necessarily concurrently, such a combination of images CTrd and Tpd, or CTrd and Tpd and Md, or Tpd and ETrd, or Tpd and ETrd and Md, or CTrd and ETrd, or CTrd and Md and ETrd, or CTrd and Tpd and Trd and Md and ETrd, or some other subcombination of all of the available images, all of which can be presented concurrently or in a selected sequence on display unit 130.

In the ET mode, the image reconstruction involves the general notion that the ultimate reconstructed slice images ETr will have improved out-of-plane spatial resolution compared to images Tr from mode T, and that images ETr will receive a greater contribution to their higher spatial frequency content from images ETp1 and a greater contribution to their lower spatial frequency content from images ETp2. To this end, the 2D projection images ETp1 and/or slice images ETr1 obtained by tomosyntesis reconstruction processing of the ETp1 images, are filtered with a high-pass filter in the spatial domain or in the frequency domain. The 2D projection images ETp2 and/or slice images ETr2 obtained by tomosyntesis reconstruction processing of the ETp2 images, are filtered with a low-pass filter in the spatial domain or in the frequency domain. The resulting filtered images are combined. For example, the high-pass filtered slice images ETr1 and the low-pass filtered images ETr2 are combined into reconstructed slice images ETr, using the appropriate geometric calculations in the reconstruction/combining process to ensure that respective slice images ETr1 and ETr2 contribute to the appropriate slice image ETr, As can be appreciated from the above discussion, in principle the projection images ETp1 that are taken when the x-ray beam is normal or near normal to the wide dimension of the compressed breast contribute mainly higher frequency content to the reconstructed slice images ETr and the remaining projection images ETp2 (which may in some examples include some or all of the images ETp1) contribute mainly the lower spatial frequency content to the reconstructed slice images ETr.

In the CT mode, image processing unit 126 carries out known operations for reconstructing the projection images CTp into slice images CTr, for example filtered backprojection in the spatial domain or in Fourier space. In the M mode, processing circuit 126 can carry out conventional operations for reducing noise or enhancing contrast. In any of the ET, T, and CT modes, processing unit 126 can further carry out processes such as using the 3D image information to generate slice images in selected different orientations that represent breast slices of different thickness, and image processing to generate synthetic mammogram images.

The 3D images resulting from the processing in console 126 can be provided for viewing or further image manipulation to a workstation 128, such as the workstation offered under the trade name SecurView by the common assignee, and/or to a display unit 130 that includes one or more computer display screens to show, at the same time, two or more of the breast images. For example, display unit 130 can show at the same time, an ETrd image together with a Tprd image and/or a Tpd image, and/or an Mpd image. Any one of these types of images can be shown as a single image, as two or more images, or in cine mode. For example, the ETrd or Trd images can be shown in cine mode changing from an image of one breast slice to an image of another slice. The images displayed at the same time can be co-registered such that the selection of an anatomical feature in one of the concurrently displayed images automatically identifies a matching anatomical feature in at least another one of the concurrently displayed images. If it is desired to immobilize and position the breast for imaging using a device different from unit 104, data acquisition system 124 can include instead a device such as a cup-shaped or funnel-shaped breast immobilizer 104' (FIG. 10), into which the breast and possibly surrounding tissue can be pulled by means such as vacuum or adhesives, and such device can be controlled by control 125 illustrated in FIG. 9. The cup or funnel would be in place of unit 104, in the imaging beam from x-ray source 108.

It can be important for a health professional to view concurrently images of a patient's breast or breasts taken with different x-ray modalities. The system disclosed in this patent specification provides that opportunity by enabling the health professional to select any desirable combinations of concurrently displayed reconstructed images CT images CTrd, reconstructed tomosynthesis slice images ETrd and Trd (including Tnrd and Twrd from the mode Tmm), the 2D projection images obtained in any of modes ET and T (including Tmm)), and mammograms Md.

Figure 10:
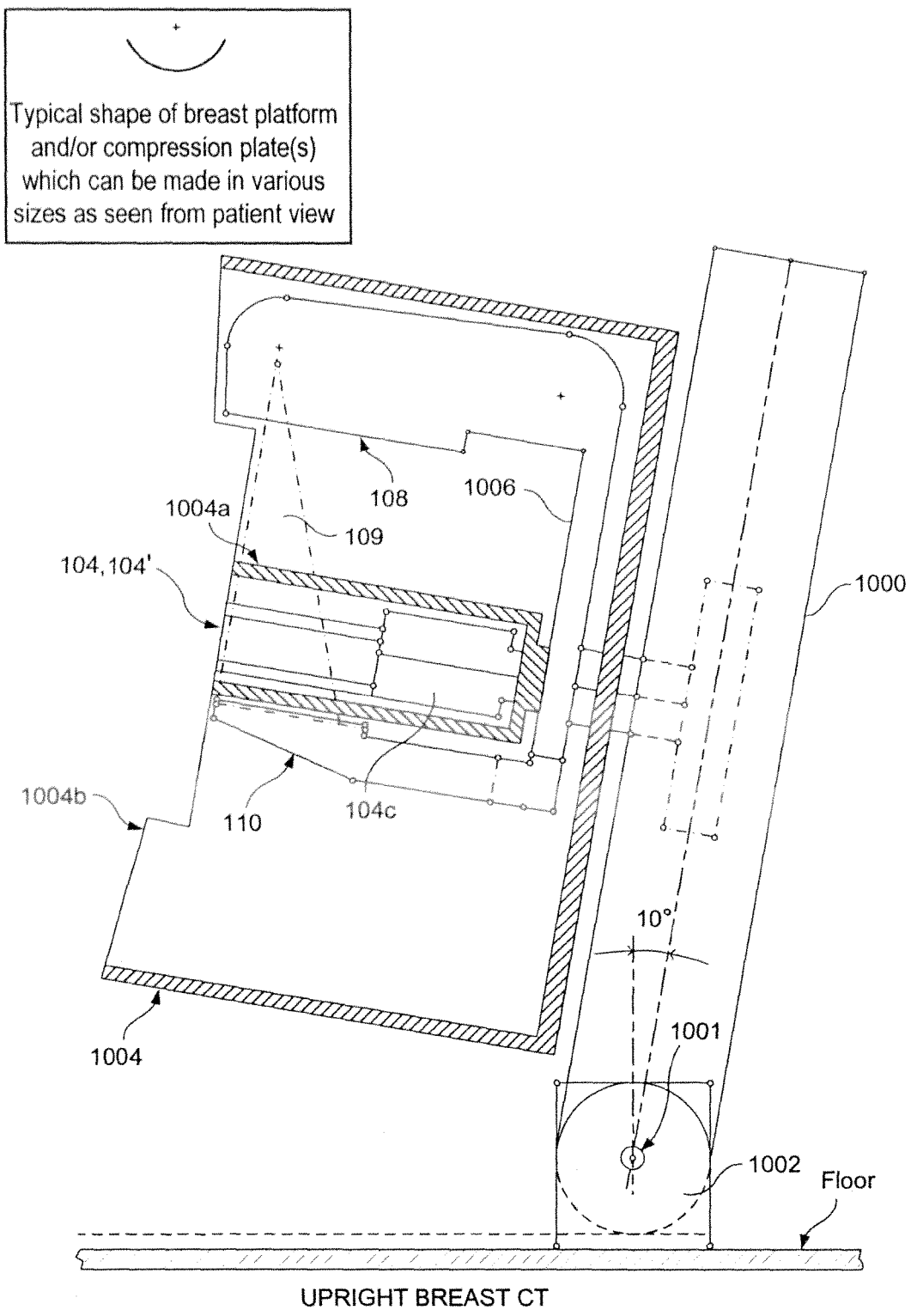
FIGS. 10 and 11 illustrate portions of an alternative embodiment improving system operation and patient comfort.

FIG. 10 illustrates another example of a system that can operate in the CT mode, as well as in any of modes ET, T (including Tmm operating in sub-modes such as of Tn and Tw), and M. A column 1000 pivots from the vertical about a horizontal pivot axis 1001 of a pivoting support 1002, for example over a 10° angle from the vertical, as illustrated, so the patient can lean forward against shield 1004. A rotating C-arm 1006 carries x-ray source 108 emitting x-ray beam 109 and an x-ray imaging receptor housing 110, and can be moved up and down column 1000 to match patients of different heights, as in the embodiments described above. Shield 1004 shields the patient from the x-ray source 108 as it rotates around breast compression unit 104, and also shields the patient from any rotational movement of x-ray imaging receptor housing 110. Shield 1004 further acts to stabilize the patient leaning against it, and may include handles that the patient holds to further facilitate patient comfort and stability. Shield 1004 can surround the rotational trajectory of source 108 and housing 110, and includes a front portion 1004b that has an opening for the patient's breast, which opening can be sufficiently large to allow a health professional to reach in to adjust the breast as it is being flattened. Shield 1004 may further include a breast platform that is between housing 110 and a portion of breast compression unit 104, on which the patient's breast can rest and be compressed by a paddle on the other side of the breast. The breast platform can be flat, or it can be shaped to the contour of a breast (e.g., the platform can be concave), and can be made in different sizes that can be changed from one patient to another. An alternative shield 1004a can be used instead of or in addition to shield 1004. Shield 1004a surrounds compression unit 104 (104'), and preferably includes a portion 1004b that also protects the patient from motion of gantry 1006. Some or all of portion 1004b may be removable, particularly for taking mammograms M.

For use in the ET mode where the source arc for ETp2 images is less than 360°, for example the arc is approximately 200°, a sector of shield 1004 can be omitted to allow space for the patient's lower body. For example, a sector of approximately 120°-160° can be omitted, in a manner similar to that discussed for FIG. 3 but at the bottom side of the shield.

Figure 11:
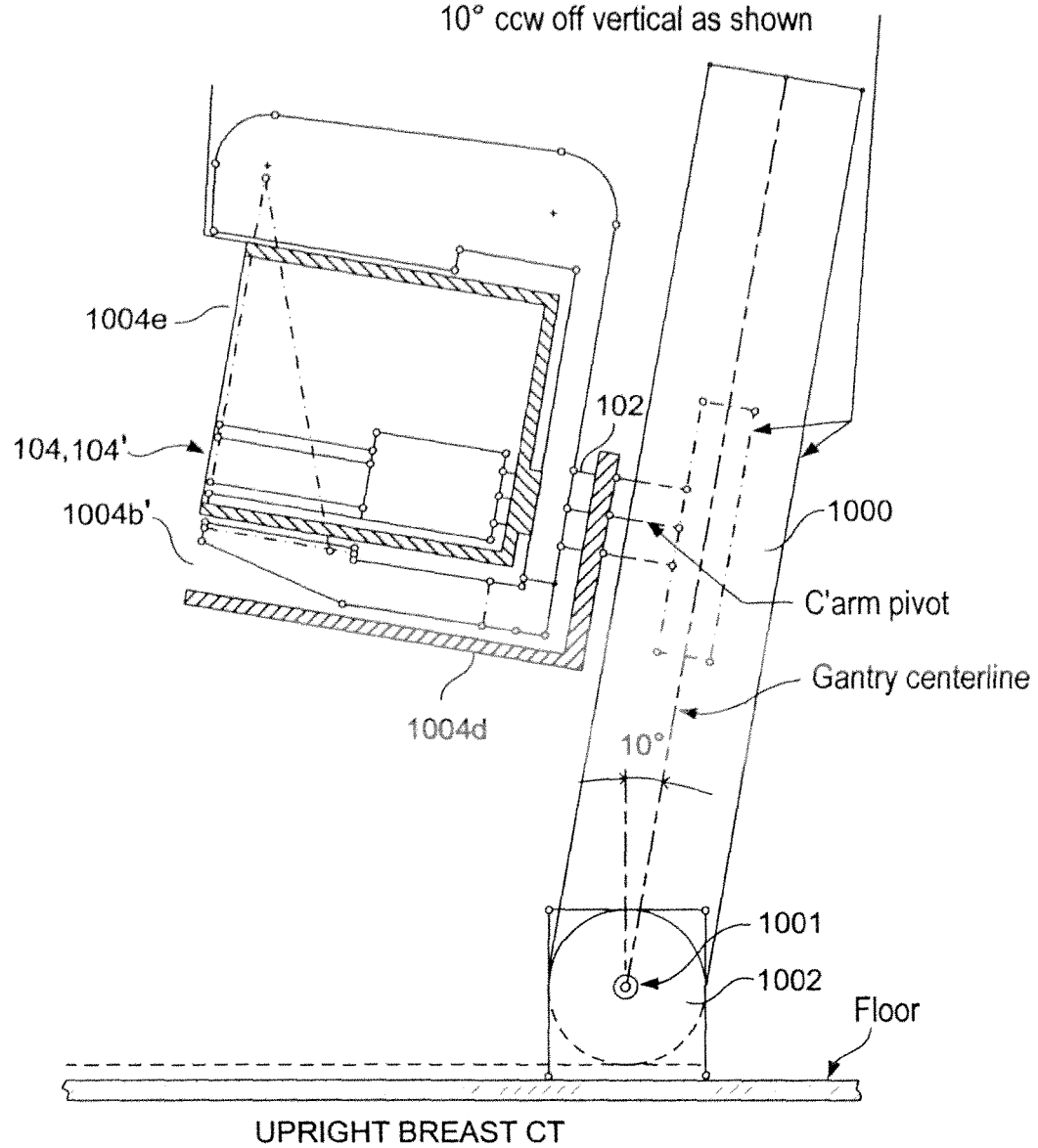

FIG. 11 illustrates another example, which is otherwise similar to that of FIG. 10 but has a differently shaped patient shield 1004d, which can be supported on axle 102, and can include a front portion 1004b' that is similar in position and function to portion 1004b in FIG. 10 but is somewhat differently shaped. As with shield 1004, shield 1004d can include a breast platform that is flat or shaped and can be in different sizes and can include patient handles. An alternative shield 1004e can be used in addition to or instead of shield 1004d, which has a different shape from shield 1004a but serves a similar purpose. The example of FIG. 11 allows greater freedom for positioning the patient's lower body relative to the x-ray system than shield 1004.

FIGS. 12-15 illustrate another example of a system that can carry x-ray breast imaging in one or more of the modes discussed above but is particularly suitable for the ET, T, and CT modes.

FIG. 12 illustrates in front elevation a patient shield 1202 that has an outer periphery 12a, a central opening 12b, and a cutout 12c in which the patient's lower body can fit. Breast immobilizer 104 is inside central opening 12b. For operation in the ET and CT modes, immobilizer 14 can be near the center of opening 12b. For operation in the T, Tmm, and M modes, immobilizer 104 is mover toward the periphery of central opening 12. For clarity, other system components are omitted from FIGS. 12 and 15 but some are shown in FIG. 13.

FIG. 13 illustrates the system of FIG. 12 in side elevation and shows some of the system components omitted from FIGS. 12 and 15. As in the systems of FIGS. 10 and 11, x-ray source 108 and receptor housing 110 are supported for rotation as a unit about breast immobilizer 104. Immobilizer 104 is mounted for radial movement in central opening 12, for example between the positions shown in FIGS. 12 and 15, and also can be mounted for rotation about its axis, for example to flatten the breast in the CC, MLO or some other orientation. Other support components of the system serve functions described earlier and bear corresponding reference numerals.

Notably, on one embodiment central opening 12b in the system of FIGS. 12-15 is much larger than necessary to receive only the patient's breast. It is sufficiently large to allow a patient to insert her arm and part of the shoulder into opening 12b such that at least a part of her axilla is in the imaging volume, this allowing not only a breast but also the breast axilla to be imaged. This is schematically illustrated in FIG. 14, where both breast 1402 and at least a part of axilla 1404 are in imaged with x-ray beam 1406. Patient's arm 1410 extend into opening 12b, and a handle 1408 or another device can be provided in opening 12b for the patient to grasp such that her arm 1410 is out of the path of moving components. Alternatively, or in addition, an internal shield can be provided in opening 12b to keep the patient's arm 1410 out of the path of moving components.

In ET and CT modes of operation, the system in the example of FIGS. 12-15 rotates source 108 and imaging receptor housing 110 about breast immobilizer 104 (when in a central position such as in FIG. 12) in the directions of the illustrated arrows and takes projection images ETp1, ETp2, and CTp as discussed above. In the T and Tmm modes, immobilizer 104 is in a position such as in FIG. 15, and imaging receptor housing 110 can similarly rotate, or is can be stationary but its internal imaging receptor can rock as in FIG. 7. In the M mode, the x-ray source and the imaging receptor are in fixed position while taking the Mp image. In any of the modes, immobilizer 104 can be rotated to position the breast in the CC orientation, or in the MLO orientation or in any other desired orientation. The projection images from the example of FIGS. 12-15 can be processed into display images as discussed above.

While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

The foregoing has been described in some detail for purposes of clarity but it will be apparent to persons skilled in the pertinent technologies that certain changes and modifications may be made without departing from the disclosed principles. There are alternative ways of implementing both the processes and apparatuses described herein that do not depart from the principles that this patent specification teaches. Accordingly, the present embodiments are to be considered as illustrative and not restrictive, and the body of work described herein is not to be limited to the details given herein, which may be modified within the scope and equivalents of the appended claims The patents and other publications, and the patent application identified above are hereby incorporated by reference in this patent specification as though fully set out herein.

As can be appreciated from the material above, the novel features of this patent specification include but are not limited to (a) CT imaging of a coronally flattened breast, including of an upright patient, (b) moving a breast immobilization unit radially within an opening between a central position for CT imaging of the breast and a position toward the periphery of the opening for tomosynthesis or mammography imaging, (c) CT and tomosynthesis imaging of a breast that is minimally compressed or in not forcibly compressed at all, and (d) blending high spatial resolution and low-spatial resolution images of a breast that are obtained in the same imaging mode and preferably in the same compression or immobilization of the breast and even images obtained in different scans of the breast.

In certain aspects, this patent specification describes an x-ray breast imaging system comprising a breast immobilizer configured to flatten a patient's breast; an x-ray source and an x-ray imaging receptor configured to image the breast in an enhanced tomosynthesis mode ET in which the receptor obtains respective two-dimensional (2D) projection tomosynthesis x-ray images ETp1 while the source traverses a first trajectory around the immobilizer and images ETp2 while the source traverses a longer second trajectory around the immobilizer; a computer-implemented image processor configured to apply tomosynthesis image reconstruction processing to the images ETp1 and ETp2 to obtain reconstructed images ETr to which the ETp1 images contribute more high spatial frequency content than the ETp2 images and which represent respective breast slices having selected thicknesses and orientations; and a display configured to display images related to said 3D reconstructed image.

The source and receptor can be further configured to alternatively or additionally operate in (a) a tomosynthesis mode T in which the source moves only in the first trajectory and only the images Tp1 are obtained and processed into breast slice images; (b) a mammography mode M in which the source and receptor remain in fixed positions relative to the breast immobilizer while the receptor generates an x-ray mammogram Mp; and (c) to rotate around the breast immobilizer while the receptor generates a multiplicity of CT projection images CTp. The T mode can include taking images Tp1 in a single motion of the source around the breast, and an alternative, multi-mode Tmm in which the system takes 2D tomosynthesis projection images Tpn over a relatively short trajectory of the source or 2D tomosynthesis projection images Tpw over a relatively long trajectory around the breast.

The receptor also can be configured to move around the breast immobilizer while obtains the 2D tomosynthesis projection images. A patient shield can be configured to enclose the moving source and the optionally moving receptor.

The patient shield can surround the first and second trajectories and can include a central opening in which the breast immobilizer is located, wherein the central opening is sufficiently large for a patient to insert her arm such that the patient axilla enters an imaging volume when the patient's breast is flattened in the breast immobilizer. The breast immobilizer can be configured to move radially within the central opening from a central position to a position near a periphery of the central opening and closer to the receptor. The patient shield that surrounds the first and second trajectories of the source can have an opening for the patient's lower body within an arc outside the source trajectories. The first trajectory can be over an arc of approximately ±7.5°, or in the range of 10°-50°, and the second trajectory can be over an arc of approximately 200°, or in the range of 50°-250°. The mammogram can be taken as in a conventional mammography system, with the source, receptor and breast stationary, or it can be synthesized from the 2D tomosynthesis images, the reconstructed slice images, or the reconstructed CT image of the breast, for example by a minimum intensity or maximum intensity projections of 3D tomosynthesis or CT information about the breast. The breast immobilizer can be configured to flatted in the breast in one of a CC orientation and an MLO orientation.

In other aspects, this patent specification describes an x-ray breast imaging system having multiple modes of operation and comprising: a breast immobilizer configured to flatten a patient's breast in an imaging volume; an x-ray source and an x-ray imaging receptor configured to selectively operate in any one of the following system modes: (a) a mammography mode M, (b) a tomosynthesis mode T (including a multi-mode Tmm in which the source trajectory or over a narrower angle path Tn or a wider angle path Tw), and (c) an enhanced tomosynthesis mode ET; wherein (a) when in mode M the system produces a mammogram image Mp taken while the source and receptor are at fixed positions relative to the immobilizer, (b) when in mode T the system produces plural two-dimensional (2D) projection images Tp each taken from a respective position of the source in a source trajectory T around the immobilizer (and in Mode Tmm produces narrower angle 3D projection images Tn1 or wider angle projection images Twp), and (c) when operating in mode ET the system produces 2D projection images ETp1 taken from respective positions of the source in a first source trajectory ET1 around the breast immobilizer and 2D projection images ETp2 taken from respective positions of the source in a second source trajectory ET2 around the immobilizer; a computer-implemented image processor configured to: (a) respond to mode M operation to process the image Mp into a display mammogram image Mpd, (b) respond to mode T operation to apply a first tomosynthesis image reconstruction processing to the images Tp (or to the images Tnp or Twp) and thereby produce reconstructed breast slice images Tr, and (c) respond to mode ET operation to apply a second tomosynthesis image reconstruction processing to the images ETp1 and ETp2 to produce reconstructed breast slice images ETr; wherein the spatial resolution at least in the breast compression direction is greater in images ETr than in images Tr; and a display configured to selectively display images derived from one or more of images Mp, Tr, and ETr. The system can include a patient shield surrounding at least the first and second source trajectories, with a central opening in which the breast immobilizer is located, which central opening is sufficiently large for a patient to insert her arm when her breast is in the breast immobilizer such that at least a part of the patient's axilla is in the imaging volume. The breast immobilizer can be configured to move between a central position in the shield opening for operation in the ET mode and a position closer to a periphery of the central opening for operation in at least one of the M mode and the T (or Tmm) mode. The immobilizer can be configured to move to the position at the periphery of the central opening for operation in each of the M and T modes. In the Tmm mode, the source trajectory in sub-mode Tn is shorter than in sub-mode Tw. The source trajectory in sub-mode Tn can be over an arc of 10°-20° and in mode Tw over an arc of 20°-50°. An anti-scatter grid can be used between the breast immobilizer and the image receptor at least in the M mode operation, but optionally can (but need not) be used also in the T (and Tmm) mode, the ET mode, and in the CT mode. The source trajectory ET1 can be over an arc of approximately 15° and the source trajectory ET2 is approximately over and arc of approximately 200°. The second tomosynthesis image reconstruction processing can be configured to include in the images ETr a greater contribution to high spatial resolution content from images ETp1 than from images ETp2 or, stated differently, a greater contribution to low spatial resolution content from images Tp2 than from images Tp1.

In other aspects, this patent specification describes an x-ray breast imaging system comprising: a breast immobilizer configured to flatten a patient's breast; an x-ray source and an x-ray imaging receptor configured to selectively image the breast in a narrow angle tomosynthesis sub-mode Tn and an a wide angle tomosynthesis sub-mode Tw, where in sub-mode Tn the receptor obtains respective two-dimensional (2D) projection tomosynthesis x-ray images Tnp while the source traverses a narrower arc trajectory around the immobilizer and in sub-mode Tw the receptor obtains respective 2D projection images Twp while the source traverses a wider arc trajectory around the immobilizer; a computer-implemented image processor configured to selectively operate in a Tn mode to apply tomosynthesis image reconstruction processing to images Tnp to reconstruct breast slice images Tnr from projection images Tnp and in a Tw mode to apply tomosynthesis reconstruction processing to images Twp to reconstruct breast slice images Twr from images Twp; and a display configured to display images related to said 3D reconstructed image. The narrower arc trajectory can be 10°-20° and the wide angle trajectory 20°-50°, or the narrower arc trajectory can be approximately 15° and the wide angle trajectory is 40°.

In other aspects, this patent specification describes an x-ray breast tomosynthesis method comprising: obtaining a first plurality of two-dimensional (2D) tomosynthesis projection images ETp1 by irradiating a patient's breast flattened in a thickness direction, from a respective plurality of first x-ray source positions distributed along a first trajectory of the source around the breast; obtaining a second plurality of two-dimensional (2D) tomosynthesis projection images ETp2 by irradiating the patient's breast from a respective plurality of second x-ray source positions distributed along a second, longer trajectory of the source around the breast; computer-processing the ETp1 and the ETp2 images into a breast slice images ETr in a tomosynthesis image reconstruction process utilizing both the ETp1 and the ETp2 images; and generating and displaying images derived from said ETr images. The reconstruction process can be configured to contribute more high spatial resolution content to images ETr from images ETp1 than from images ETp2. The first trajectory can be over an arc of approximately 15° and the source trajectory ET2 over and arc of approximately 200°. The first trajectory can over an arc of 10°-20° and the second trajectory over and arc of 25°-250°. The method can include shielding the patient from the source motion along both the first and second trajectories, and inserting in an imaging volume both the patient's breast and the patient's arm and at least a part of the patient's axilla. The method can include selectively imaging the flattened patient's breast in any one of (a) an ET mode that comprises obtaining images ETp1 and ETp2, (b) a tomosynthesis mode T that comprises obtaining 2D projection images Tp in the course of source motion along a single trajectory (and includes a mode Tmm obtaining tomosynthesis 2D projection images Tnp over a narrower angle source trajectory or tomosynthesis 2D projection images Twp over a wider angle source trajectory), and (c) a mammography mode M that comprises obtaining a mammogram Mp with the source in a fixed position relative to the flattened breast.

In still other aspects, this patent specification describes a computer program stored in non-transitory form on a computer-readable medium, which program when executed in a computer system causes computerized equipment to carry out the steps of: obtaining a first plurality of two-dimensional (2D) tomosynthesis projection images ETp1 from irradiating a patient's breast flattened in a thickness direction, from a respective plurality of first x-ray source positions distributed along a first trajectory of the source around the breast; obtaining a second plurality of two-dimensional (2D) tomosynthesis projection images ETp2 from irradiating the patient's breast from a respective plurality of second x-ray source positions distributed along a second, longer trajectory of the source around the breast; processing the ETp1 and the ETp2 images into breast slice images ETr through a tomosynthesis image reconstruction process utilizing both the ETp1 and the ETp2 images; and generating and displaying images derived from said 3D representation of the breast. The processing can comprise including in the images ETr a greater contribution to high spatial resolution from images ETp1 than from images ETp2. The first trajectory can be over an arc of 10°-20° and the second trajectory over and arc of 25°-250°.

The invention claimed is:

1. An x-ray breast imaging system comprising:
a breast immobilizer configured to flatten a patient's breast;
an x-ray source and an x-ray imaging receptor configured to image the breast in an enhanced tomosynthesis mode ET in which the receptor obtains a first set of two-dimensional (2D) projection tomosynthesis x-ray images ETp1 for a first trajectory of the source around the immobilizer and a second set of images ETp2 for a longer second trajectory of the source around the immobilizer;
a computer-implemented image processor configured to apply tomosynthesis image reconstruction processing to the images ETp1 and ETp2 to obtain reconstructed images ETr, wherein one of the sets of (i) ETp1 images and (ii) ETp2 images contributes more high spatial frequency content than the other set to the reconstructed images ETr, and the images Etr represent respective breast slices having selected thicknesses and orientations; and
a display configured to display images related to said 3D reconstructed images ETr.

2. The system of claim 1, in which the source and receptor are further configured to alternatively operate in a tomosynthesis mode T in which the source moves only in the first trajectory and only the images Tp1 are obtained and processed into breast slice images.

3. The system of claim 1, in which the source and receptor are further configured to alternatively operate in a mammography mode M in which the source and receptor remain in fixed positions relative to the breast immobilizer while the receptor generates an x-ray mammogram Mp.

4. The system of claim 1, in which the source and receptor are further configured to rotate around the breast immobilizer while the receptor generates a multiplicity of CT projection images CTp.

5. The system of claim 1, in which both the source and the receptor are configured to move around the breast immobilizer in the course of the receptor obtaining the ETp2 images, and further including a patient shield configured to enclose the moving source and receptor.

6. The system of claim 1, including a patient shield that surrounds the first and second trajectories and has a central opening in which the breast immobilizer is located, wherein the central opening is sufficiently large for a patient to insert her arm therein such that at least a significant portion of a patient axilla enters an imaging volume when the patient's breast is flattened in the breast immobilizer.

7. The system of claim 6, in which the breast immobilizer is configured to move radially within the central opening between a central position and a position nearer a circumferential periphery of the central opening and closer to the receptor.

8. The system of claim 1, including a patient shield that surrounds the first and second trajectories of the source and has an opening for the patient's lower body within an arc outside the source trajectories.

9. The system of claim 1, in which the second trajectory is over a 60° arc.

10. The system of claim 1, in which the image processor is further configured to generate a synthetic mammogram of the breast from projection tomosynthesis images.

11. An x-ray breast imaging system having multiple modes of operation comprising:
a breast immobilizer configured to flatten a patient's breast in an imaging volume;
an x-ray source and an x-ray imaging receptor configured to selectively operate in any one or more of the following system modes while the breast remains in the immobilizer: (a) a mammography mode M, (b) a tomosynthesis mode T, and (c) an enhanced tomosynthesis mode ET;
wherein (a) when in mode M the system produces a mammogram image Mp taken while the source and receptor are at fixed positions relative to the immobilizer, (b) when in mode T the system produces plural two-dimensional (2D) projection images Tp each taken from a respective position of the source in a source trajectory T around the immobilizer, and (c) when operating in mode ET the system produces 2D projection images ETp1 taken from respective positions of the source in a first source trajectory ET1 around the breast immobilizer and 2D projection images ETp2 taken from respective positions of the source in a second source trajectory ET2 around the immobilizer that is longer than the first source trajectory;

a computer-implemented image processor configured to: (a) respond to mode M operation to process the image Mp into a display mammogram image Mpd, (b) respond to mode T operation to apply a first tomosynthesis image reconstruction processing to the images Tp and thereby produce reconstructed breast slice images Tr, and (c) respond to mode ET operation to apply a second tomosynthesis image reconstruction processing to the images ETp1 and ETp2 to produce reconstructed breast slice images ETr;

wherein the spatial resolution at least in a breast compression direction is greater in one of images Tr and ETr than in the other of images Tr and ETr; and a display configured to selectively display images derived from one or more of images Mp, Tr, and ETr.

12. The system of claim 11, including a patient shield surrounding at least the first and second trajectories, which patient shield has a central opening in which the breast immobilizer is located and which is sufficiently large for a patient to insert her arm when her breast is in the breast immobilizer such that at least a significant part of a patient's axilla is in the imaging volume.

13. The system of claim 11, in which the breast immobilizer is configured to move between a central position in the shield opening for operation in the ET mode and a position at a circumferential periphery of the central opening for operation in at least one of the M mode and the T mode.

14. The system of claim 11, including an anti-scatter grid between the immobilizer and the receptor in at least one of the T mode operation and the ET mode operation.

15. The system of claim 11, in which the x-ray source and x-ray imaging receptor are further configured to selectively operate in a CT mode to generate reconstructed slice or volume images CTr of the breast and the display is configured to selectively display images derived from each of images Mp, Tp, Tr, ETr, and CTr.

16. An x-ray breast imaging system comprising:

a breast immobilizer configured to flatten a patient's breast; and an x-ray source and an x-ray imaging receptor configured to image the breast in a tomosynthesis mode T in which the receptor obtains a set of two-dimensional (2D) projection tomosynthesis x-ray images Tp of a patient's breast in the immobilizer and a set of computerized tomography (CT) projection images CTp of the patient's breast in the immobilizer;

wherein said x-ray source and said x-ray receptor are configured to acquire both said set of tomosynthesis images Tp and said set of CT images CTp while the patient's breast remains flattened in the immobilizer.

17. The system of claim 16, in which the x-ray source and the x-ray receptor are configured to acquire both the first set of images Tp and the second set of images CTp in a single scan of the x-ray source around the immobilizer.

18. The system of claim 16, in which the x-ray source and the x-ray receptor are configured to acquire the images Tp in a first scan of the x-ray source around the immobilizer and to acquire the images CTp in a second scan of the x-ray source around the immobilizer that is spaced in time from the first scan.

19. The system of claim 16, in which the x-ray source, the x-ray receptor, and the immobilizer are configured to acquire both the images Tp and the images CTp while the patient is upright.

20. The system of claim 16, in which the trajectories of the x-ray source rotation around the breast immobilizer for acquiring the images Tp and the images CTp overlap at least partly.

* * * * *

UNITED STATES PATENT AND TRADEMARK OFFICE
CERTIFICATE OF CORRECTION

PATENT NO. : 10,098,601 B2
APPLICATION NO. : 15/597713
DATED : October 16, 2018
INVENTOR(S) : Andrew P. Smith et al.

It is certified that error appears in the above-identified patent and that said Letters Patent is hereby corrected as shown below:

On the Title Page

(72) Inventors should read:
Andrew P. SMITH, Lexington, MA (US);
Jay A. STEIN, Boston, MA (US);
Ken DEFREITAS, Patterson, NY (US);
Ian SHAW, Yorktown Heights, NY (US);
Zhenxue JING, Chadds Ford, PA (US);
Lauren NIKLASON, N. Tetonia, ID (US);
Baorui REN, Andover, MA (US);
Christopher RUTH, Boxford, MA (US)

Signed and Sealed this
Thirtieth Day of August, 2022

Katherine Kelly Vidal
*Director of the United States Patent and Trademark Office*